(12) United States Patent
Evans et al.

(10) Patent No.: US 12,275,011 B2
(45) Date of Patent: Apr. 15, 2025

(54) TISSUE SAMPLE CONTAINERS AND RELATED METHODS

(71) Applicant: Leavitt Medical, Inc., Lehi, UT (US)

(72) Inventors: Mark S. Evans, Holladay, UT (US); Michael Andrew Ivie, Orem, UT (US)

(73) Assignee: Leavitt Medical, Inc., Lehi, UT (US)

( * ) Notice: Subject to any disclaimer, the term of this patent is extended or adjusted under 35 U.S.C. 154(b) by 0 days.

(21) Appl. No.: 18/329,136

(22) Filed: Jun. 5, 2023

(65) Prior Publication Data

US 2023/0311129 A1 Oct. 5, 2023

Related U.S. Application Data

(60) Continuation of application No. 17/523,107, filed on Nov. 10, 2021, now Pat. No. 11,707,740, which is a
(Continued)

(51) Int. Cl.
| | |
|---|---|
| *B01L 1/00* | (2006.01) |
| *A61B 10/00* | (2006.01) |
| *B01L 3/00* | (2006.01) |
| *G01B 11/02* | (2006.01) |
| *G01B 11/06* | (2006.01) |
| *G01B 11/28* | (2006.01) |

(Continued)

(52) U.S. Cl.
CPC ........ *B01L 3/5085* (2013.01); *A61B 10/0096* (2013.01); *B01L 3/50853* (2013.01); *G01B 11/022* (2013.01); *G01B 11/0608* (2013.01); *G01B 11/285* (2013.01); *G01N 21/03* (2013.01); *G01N 35/00732* (2013.01); *G06V 20/693* (2022.01); *B01L 2300/02* (2013.01); *B01L 2300/021* (2013.01); *B01L 2300/022* (2013.01); *B01L 2300/041* (2013.01); *B01L 2300/069* (2013.01); *G01N 2035/00752* (2013.01); *G01N 2035/00772* (2013.01)

(58) Field of Classification Search
None
See application file for complete search history.

(56) References Cited

U.S. PATENT DOCUMENTS

| | | | |
|---|---|---|---|
| 5,061,452 | A | 10/1991 | Yamamoto |
| 5,427,742 | A | 6/1995 | Holland |

(Continued)

FOREIGN PATENT DOCUMENTS

| | | |
|---|---|---|
| CA | 3077375 A1 | 3/2019 |
| CN | 111417348 A | 7/2020 |

(Continued)

OTHER PUBLICATIONS

Extended European Search Report for European Patent Application No. 18850235.5, mailed Sep. 8, 2021; 14 pages.
(Continued)

*Primary Examiner* — Jyoti Nagpaul
(74) *Attorney, Agent, or Firm* — Greenberg Traurig, LLP (57) ABSTRACT

Tissue sample cassettes for receiving tissue samples include an upper tray including compartments separated by dividers, a lower tray coupled to the upper tray and having a central recess, and an absorbent material located in the recess of the lower tray. Related systems and methods for automated gross processing of tissue samples are also disclosed.

18 Claims, 5 Drawing Sheets

Related U.S. Application Data division of application No. 16/115,990, filed on Aug. 29, 2018, now Pat. No. 11,173,489.

(60) Provisional application No. 62/551,683, filed on Aug. 29, 2017.

(51) Int. Cl.
*G01N 21/03* (2006.01)
*G01N 35/00* (2006.01)
*G06V 20/69* (2022.01)

(56) References Cited

U.S. PATENT DOCUMENTS

| | | | |
|---|---|---|---|
| 5,609,827 | A | 3/1997 | Russell |
| 5,817,032 | A | 10/1998 | Williamson, IV |
| 5,928,934 | A | 7/1999 | McCormick |
| 6,258,327 | B1 | 7/2001 | Tatum |
| 7,156,814 | B1 | 1/2007 | Williamson, IV |
| 8,163,252 | B2 | 4/2012 | Booker |
| 8,329,120 | B2 * | 12/2012 | Williamson, IV ............ G01N 33/4833 206/486 |
| 8,383,067 | B2 | 2/2013 | Williamson, IV |
| 8,463,741 | B2 | 6/2013 | Ehlke |
| 8,822,224 | B2 | 9/2014 | Markin |
| 9,052,256 | B2 | 6/2015 | Knorr |
| 9,097,629 | B2 | 8/2015 | Boehl |
| 9,250,253 | B2 | 2/2016 | Markin |
| 9,409,164 | B2 | 8/2016 | Tawfik |
| 9,492,130 | B2 | 11/2016 | Flagle |
| 9,633,176 | B2 | 4/2017 | De La Torre-Bueno |
| 2002/0162843 | A1 | 11/2002 | Alley |
| 2004/0052408 | A1 | 3/2004 | Sharman |
| 2005/0112034 | A1 | 5/2005 | McCormick |
| 2007/0116612 | A1 | 5/2007 | Williamson, IV |
| 2008/0227144 | A1 | 9/2008 | Nightingale |
| 2008/0318265 | A1 | 12/2008 | Visinoni |
| 2009/0246825 | A1 | 10/2009 | McCormick |
| 2010/0167334 | A1 | 7/2010 | Williamson, IV |
| 2010/0167338 | A1 | 7/2010 | Amano |
| 2012/0149049 | A1 | 6/2012 | Torres |
| 2014/0135236 | A1 * | 5/2014 | Musat .................... G01N 1/36 506/18 |
| 2016/0085913 | A1 | 3/2016 | Evans |
| 2016/0245833 | A1 | 8/2016 | Lefebvre |
| 2019/0060893 | A1 | 2/2019 | Evans |
| 2022/0062892 | A1 | 3/2022 | Evans |
| 2023/0311129 | A1 | 10/2023 | Evans |

FOREIGN PATENT DOCUMENTS

| | | |
|---|---|---|
| EP | 3675743 A2 | 7/2020 |
| KR | 20200062207 A | 6/2020 |
| WO | 2008073387 A1 | 6/2008 |
| WO | 2019046466 A4 | 3/2019 |

OTHER PUBLICATIONS

Farcas et al., "A New Method for Simultaneous Processing and Analysis of Prostate Core Biopsies", presented at the 2nd Congress of the Societe Internationale d'Urologie, Sep. 30, 2012, Fukuoka, Japan; 1 page.

Final Office Action for U.S. Appl. No. 16/115,990 mailed Jan. 22, 2021; 18 pages.

First Examination Report for Indian Patent Application serial No. 202017013233, mailed Feb. 8, 2022; 6 pages.

International Preliminary report on Patentability for International Application No. PCT/US2018048608, mailed Sep. 3, 2019; 20 pages.

International Search Report and Written Opinion for International Appplucation No. PCT/US2018048608, mailed Feb. 27, 2019; 14 pages.

Non-Final Office Action for U.S. Appl. No. 16/115,990 mailed Apr. 23, 2021; 16 pages.

Non-Final Office Action for U.S. Appl. No. 16/115,990 mailed Aug. 6, 2020; 28 pages.

Notice of Allowance for U.S. Appl. No. 16/115,990 mailed Aug. 9, 2021; 26 pages.

Office Action for Canadian Patent Application Serial No. 3077375, mailed Aug. 30, 2024; 5 pages.

Partial Supplementary Search Report for European Patent Application No. 18850235.5, mailed Jun. 22, 2021, 15 pages.

* cited by examiner

TISSUE SAMPLE CONTAINERS AND RELATED METHODS

CROSS-REFERENCE TO RELATED APPLICATION

This application is a continuation of U.S. patent application Ser. No. 17/523,107, filed Nov. 10, 2021, titled "SYSTEMS FOR GROSS PROCESSING OF TISSUE SAMPLES AND RELATED METHODS," which is a divisional of U.S. patent application Ser. No. 16/115,990, filed Aug. 29, 2018, titled "BIOPSY TISSUE SAMPLE CASSETTE AND RELATED SYSTEMS AND METHODS," which claims the benefit of U.S. Provisional Patent Application No. 62/551,683, filed Aug. 29, 2018, titled "BIOPSY TISSUE SAMPLE CASSETTE AND RELATED SYSTEMS AND METHODS," the entire disclosure of each of which is hereby incorporated by this reference.

FIELD

Embodiments of the application relate to biopsy tissue sample cassettes for gross processing of tissue samples within the tissue sample cassettes, including related systems and methods.

BACKGROUND

In biopsy processes, tissue samples are taken from a patient and placed in one or more compartments of a tissue sample cassette. The tissue sample cassette is often placed in a container containing formalin (an aqueous formaldehyde solution) or another liquid for chemical fixation and/or transportation to a pathology laboratory, where further processing (e.g., histology, grossing, fixation, dehydration, infiltration, embedding, microtome sectioning, staining, microscopic review) of the tissue sample may take place. Alternatively, the tissue samples may be transported in one or more formalin-filled bottles.

For some biopsy procedures, such as some needle-core biopsies, multiple tissue samples are obtained from a patient's organ or other body area and placed into respective tissue sample cassettes. When the pathology laboratory receives the container including the tissue samples, the specimen is typically logged into a manual or computerized anatomic pathology system and may be assigned a tracking number. This tracking number may be manually recorded or may be in the form of a bar code on a label or sticker applied to biopsy containers and tissue preparation cassettes. As the specimen is logged into the system, a physical description is provided by a pathologist or an assistant as part of the gross examination or "grossing" portion of processing the specimen.

SUMMARY

As will be described in greater detail below, the present disclosure describes devices, systems, and methods for tissue sample processing, such as for pathological procedures.

In one embodiment, the present disclosure includes tissue sample cassettes that include an upper tray with compartments separated by dividers in a top wall of the upper tray, a lower tray coupled to the upper tray, and an absorbent material located in a central recess of the lower tray. The central recess may be defined by sidewalls located on a base of the lower tray. The dividers of the upper tray may be located over an upper surface of the absorbent material. The compartments may be sized and configured to retain tissue samples therein and over the upper surface of the absorbent material.

In some examples, the tissue sample cassette may further include a cover releasably secured to at least one of the upper tray or the lower tray. The cover may include indentations in an upper surface thereof. The indentations may be sized and configured to respectively at least partially extend into the compartments of the upper tray. At least a portion of a lower surface of the cover proximate the upper tray may include a hydrophobic material. At least a portion of the upper surface of the absorbent material may include a hydrophilic material. Each of the cover and the lower tray may include at least one tab to facilitate removal of the cover from the lower tray. The dividers of the upper tray may include sidewalls including depth markers. Each of the compartments may include an elongated opening in the top wall of the upper tray and a recess in a front wall configured to facilitate placement of the tissue samples on the upper surface of the absorbent material through the elongated opening. The inner sidewalls of the dividers of the upper tray may include an upper vertical portion, a lower vertical portion, and an inclined portion between the upper vertical portion and the lower vertical portion. The upper tray may also include a front wall, a back wall opposite the front wall, a first sidewall, and a second sidewall opposite the first sidewall. The top wall of the upper tray may extend between the front wall, the back wall, the first sidewall, and the second sidewall. The top wall of the upper tray may also include alphanumeric indicators corresponding to the compartments. Each of the alphanumeric indicators may be located on the top wall of the upper tray between the back wall of the upper tray and a distal end of a respective compartment.

In one example, the absorbent material may include an upper surface with at least one cutout sized and shaped for receiving a tissue sample therein. The tissue sample cassette may also include a tracking element. The tracking element may be located on a lower surface of a base portion of the lower tray. The tracking element may be selected from the group consisting of a radio-frequency identification (RFID) tag, a barcode label, a written label, and a serial number label. The absorbent material may include a pre-wetted sponge. A material forming the tissue sample cassette may be resistant to degradation when exposed to at least one of formalin, an RNA preservative, saline solution, a chemical fixative, and/or water. In one example, the compartments of the upper tray may each include an elongated compartment sized to receive a needle-core biopsy tissue sample.

In some embodiments, the present disclosure includes systems for automated gross processing of tissues samples in a tissue sample cassette. Such systems may include a multi-compartment tissue sample cassette including a tracking element, at least one imaging device, a tracking element reader, and a processor. The at least one imaging device may be configured to obtain images of tissue samples positioned within respective compartments of the multi-compartment tissue sample cassette. The tracking element reader may be associated with the at least one imaging device and may be configured to read information from the tracking element of the multi-compartment tissue sample cassette. The processor may be associated with the at least one imaging device and the tracking element reader. The processor may be in communication with memory configured to store the images of the tissue samples. The processor may be programmed to recognize the tissue samples and to determine and provide gross measurements for the tissue samples based on the images of the tissue samples obtained with the at least one imaging device.

In some examples, the processor may be configured to accept information associated with the tracking element being read by the tracking element reader. The processor may be configured to process information associated with records stored in a data storage unit. The gross measurements provided by the processor may include at least one of height, length, or area of the tissue samples.

In some embodiments, the present disclosure includes methods of providing gross measurements of tissue samples in a tissue sample cassette. In accordance with such methods, tissue samples may be supported with a multi-compartment tissue sample cassette. At least one image of the tissue samples may be acquired utilizing an imaging device. Gross measurements of the tissue samples may be determined using a processor programmed to recognize the tissue samples from the at least one image and to provide the gross measurements based on the at least one image.

In some examples, the acquired at least one image and the gross measurements may be linked with records using a tracking element reader configured to recognize a tracking element associated with the multi-compartment tissue sample cassette. The tissue samples may be transported with the tissue sample cassette to a pathology laboratory without the tissue samples being suspended in a fluid. In one example, a plurality of images of the tissue samples may be acquired with at least one camera. In one example, the processor may be used to recognize tissue samples based on the acquired images and based at least in part on information stored in a data storage unit.

BRIEF DESCRIPTION OF THE DRAWINGS

The accompanying drawings illustrate a number of example embodiments and are a part of the specification. Together with the following description, these drawings demonstrate and explain various principles of the present disclosure.

FIGS. 1-8 illustrate various views of a tissue sample cassette according to an embodiment of the disclosure.

DETAILED DESCRIPTION OF EXAMPLE EMBODIMENTS

The embodiments of the disclosure include tissue sample cassettes for transportation and/or other processing of tissue samples for biopsy and pathological procedures. The tissue sample cassettes may include multiple compartments, such as individualized compartments (e.g., wells or cavities) sized and configured for retention of collected tissue samples. The tissue sample cassettes may contain absorbent material containing a volume of liquid, such as formalin and/or an RNA preservative, accessible to the individualized compartments of the tissue sample cassette for fixation and/or preservation of the tissue samples retained therein. The compartments may also be configured to facilitate an automated grossing process, wherein an imaging system is utilized to obtain images, measure dimensions of the tissue samples based on the obtained images, record collected data, and prepare images of the tissue samples in order to expedite the grossing process and subsequent pathology procedures. As used herein, the term "and/or" includes any and all combinations of one or more of the associated listed items.

Figure 1:
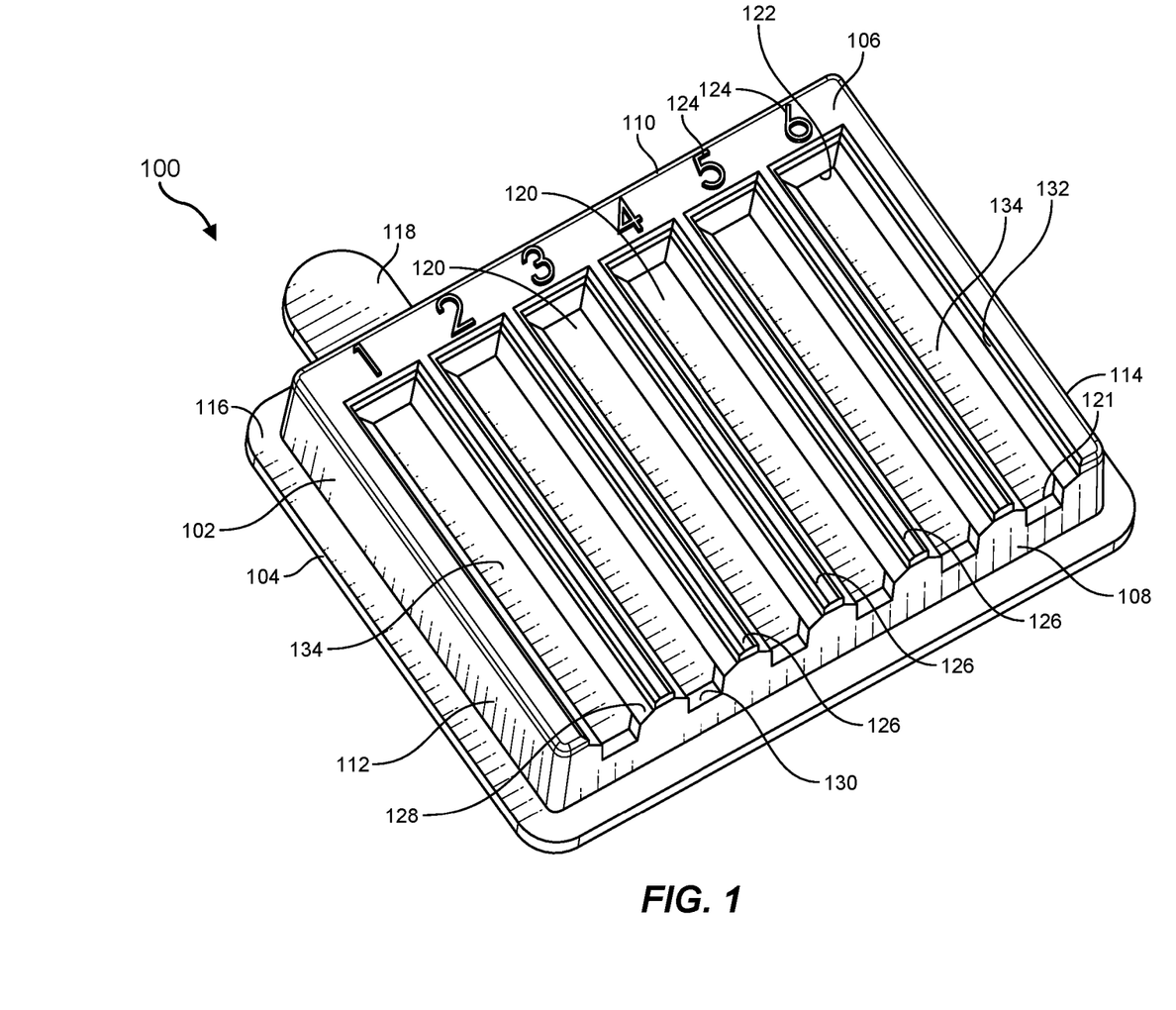
FIG. 1 shows a top perspective view of the tissue sample cassette according to an embodiment of the disclosure.
Figure 2:
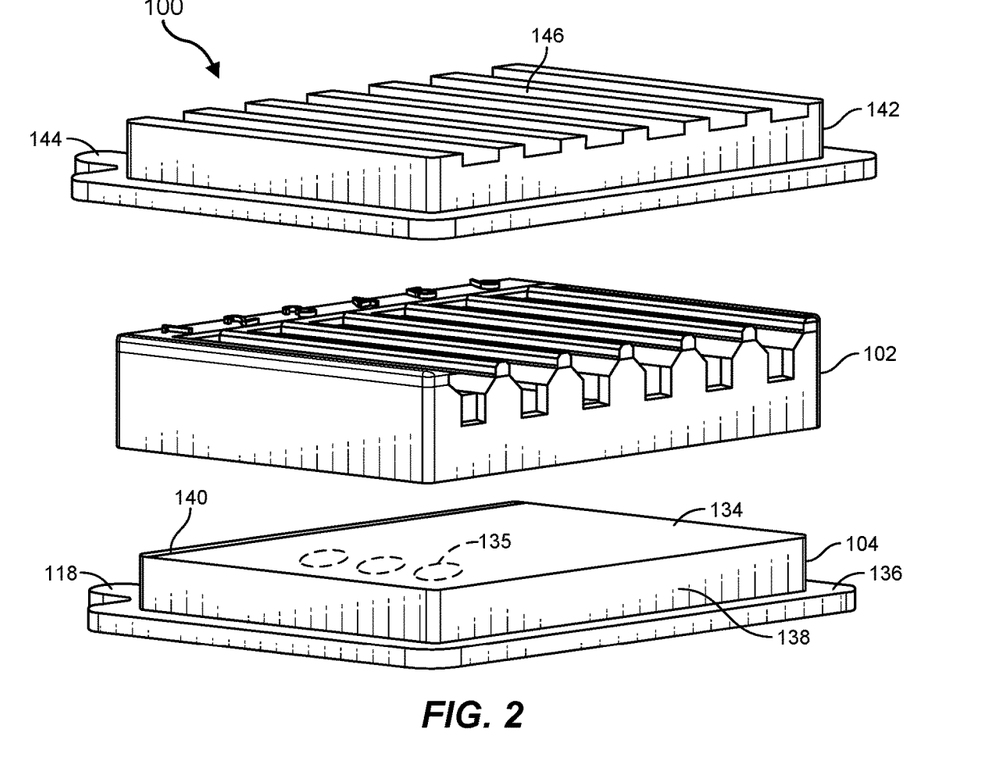
FIG. 2 shows an exploded top perspective view of the tissue sample cassette of FIG. 1.
Figure 3:
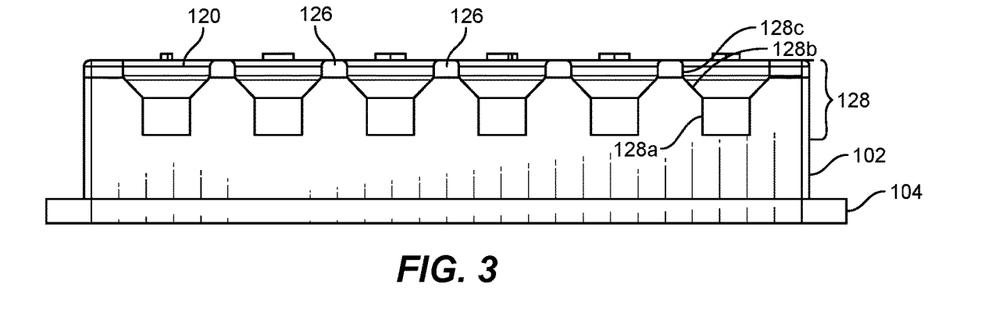
FIG. 3 shows a front view of the tissue sample cassette of FIG. 1.
Figure 4:
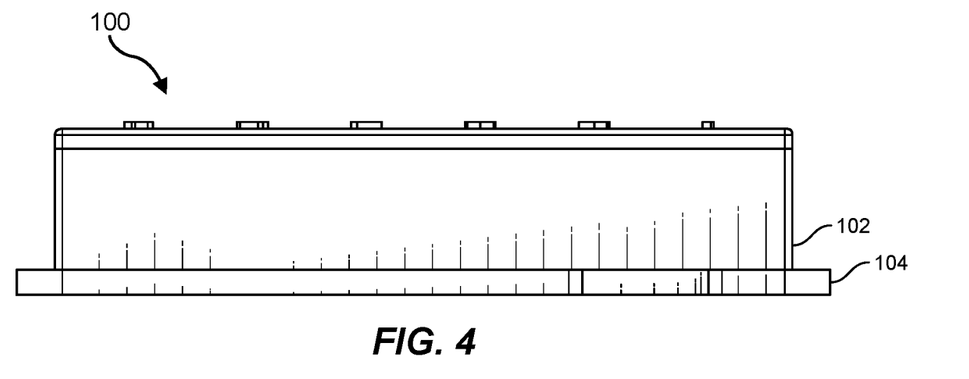
FIG. 4 shows a back view of the tissue sample cassette of FIG. 1.
Figure 5:
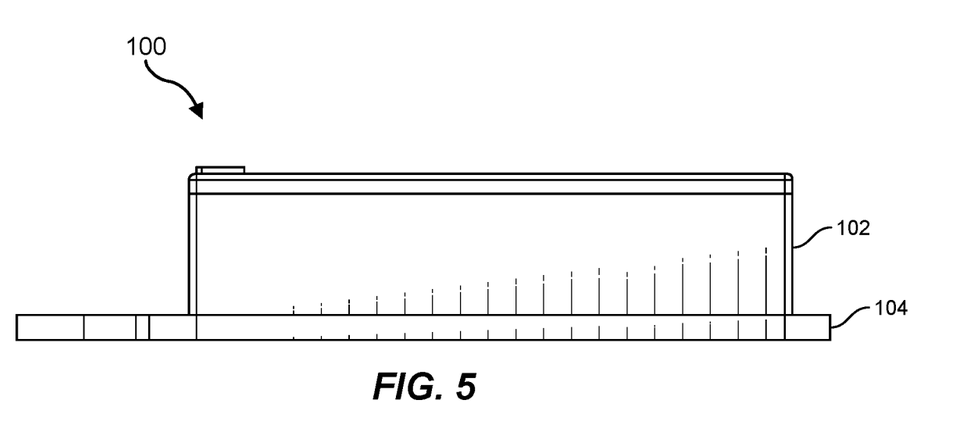
FIG. 5 shows a left side view of the tissue sample cassette of FIG. 1.
Figure 6:
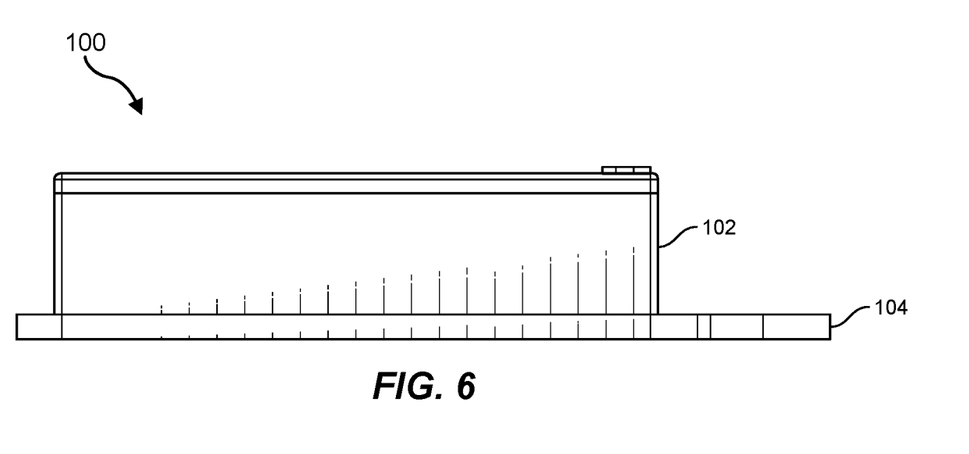
FIG. 6 shows a right side view of the tissue sample cassette of FIG. 1.
Figure 7:
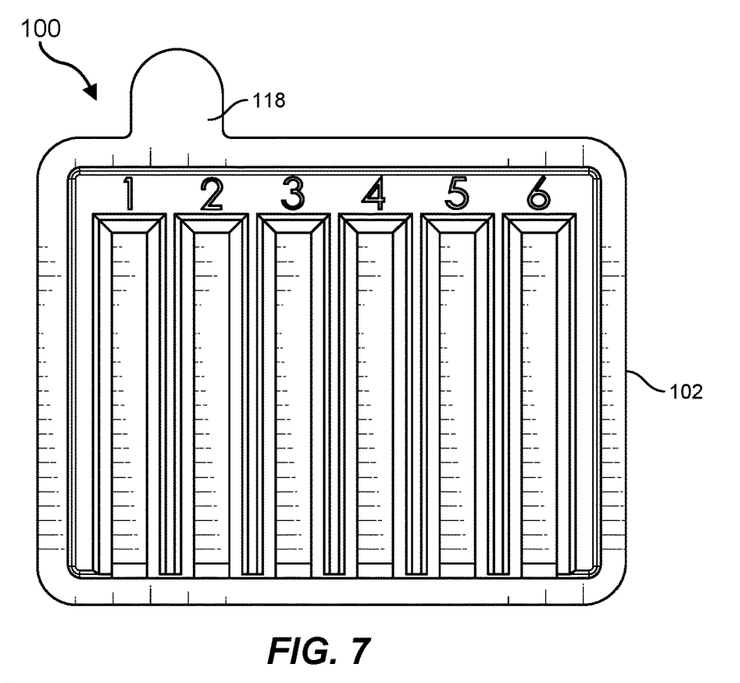
FIG. 7 shows a top plan view of the tissue sample cassette of FIG. 1.
Figure 8:
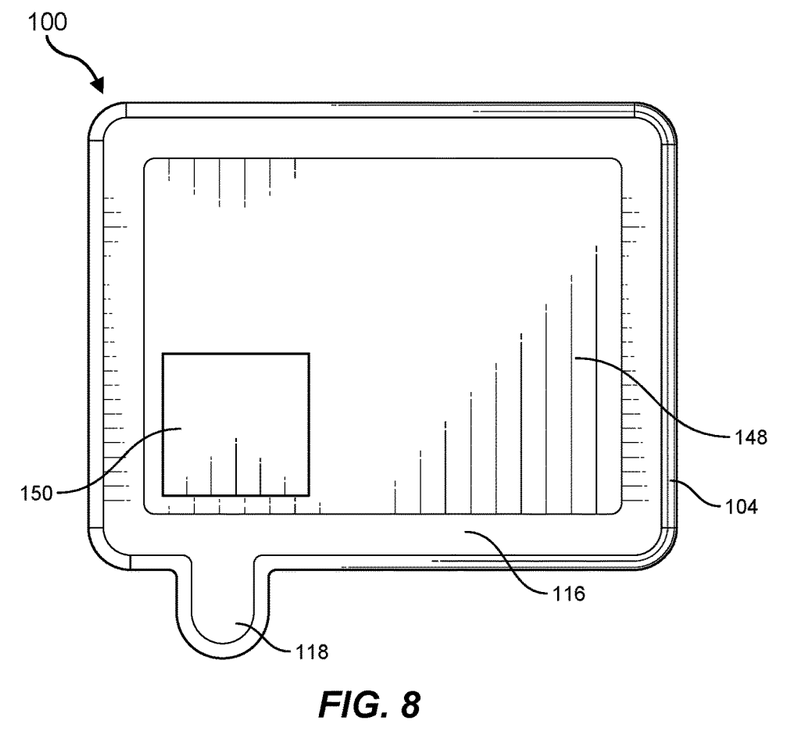
FIG. 8 shows a bottom view of a tissue sample cassette of FIG. 1.

FIG. 1 shows a top perspective view of a tissue sample cassette 100 (also referred to herein as "cassette 100" for simplicity) for biopsy and pathology transportation and/or processing according to an embodiment of the disclosure. FIG. 2 shows an exploded top perspective view of the cassette 100 of FIG. 1 and FIG. 3 shows a front view of the cassette 100. In addition, FIG. 4 shows a back view of the cassette 100, FIG. 5 shows a left side view, FIG. 6 shows a right side view, FIG. 7 shows a top plan view, and FIG. 8 shows a bottom view of the cassette 100.

Referring to FIGS. 1-3, the tissue sample cassette 100 may include a generally rectangular structure including an upper tray 102, a lower tray 104, and a cover 142 (shown in FIG. 2). In some embodiments, each of the upper tray 102, the lower tray 104, and the cover 142 may be separate components, each component of the cassette 100 being sized and configured to be releasably secured to one another and collectively referred to as the tissue sample cassette 100. For example, the upper tray 102 may be releasably secured to the lower tray 104 using a friction fit, retention slots, clips, or other such engagement members. Similarly, the cover 142 may be releasably secured to the upper tray 102 and/or to the lower tray 104. The upper tray 102 of the cassette 100 may include a top wall 106 extending between a front wall 108 and a back wall 110 opposite the front wall 108. In addition, the top wall 106 may extend between a first sidewall 112 and a second sidewall 114 opposite the first sidewall 112.

The lower tray 104 may include a base portion 116 and a recess 140 defined by sidewalls 138 extending upward from an upper surface 136 of the base portion 116. The recess 140 of the lower tray 104 may be sized and configured for retaining an absorbent material 134 (e.g., a pre-wetted sponge) to facilitate retention and preservation of a tissue sample to be positioned thereon. The absorbent material 134 may contain an RNA-preserving solution, for example, a solution comprising an aqueous solvent and an RNA preservative. Alternatively or additionally, another volume of liquid, such as formalin, saline solution, a chemical fixative, and/or water, may be disposed within the recess 140 to at least partially saturate the absorbent material 134. The sidewalls 138 of the lower tray 104 may define a generally rectangular structure that may be sized and configured to be slidably retained within and proximate a complementary generally rectangular structure defined by each of the front wall 108, the back wall 110, the first sidewall 112, and the second sidewall 114 of the upper tray 102. In other words, the two generally rectangular structures may be slidably engaged with another when the cassette 100 is assembled. Further, the upper tray 102 and the lower tray 104 may provide a water-tight or water-resistant seal around the sidewalls thereof when assembled.

The cassette 100 may be formed of any material that is compatible with (e.g., not reactive with) liquids to which the cassette 100 may be exposed, such as formalin, an RNA preservative, saline solution, a chemical fixative, or water. By way of example, the cassette 100 may be formed of a polymer material (e.g., thermosetting polymers, thermoplastic polymers, polyethylene, polyvinyl chloride, polypropylene, polystyrene, polycarbonate, acetal, silicone), a metal material (e.g., aluminum, stainless steel), or a composite material (e.g., fiberglass, carbon fiber composite, aramid fiber composite). Further, at least the cover 142 may be clear (e.g., transparent) for imaging of tissue samples therethrough, as discussed in further detail below. By way of example and not limitation, the cassette 100 may be manufactured by injection molding, machining, extruding, thermoforming, 3D printing, or a combination of such processes. The cassette 100 may be one integral piece or multiple pieces that are secured together. For example, components of the cassette 100 may be constructed to be form fitted (e.g., vacuum formed over a mold) to ensure like sizes and shapes among components. In some embodiments, the cassette 100 may be manufactured by extrusion followed by machining or stamping, by injection molding, by 3D printing, by casting, or by machining, for example.

The base portion 116 of the lower tray 104 may further include a tab 118 for ease of grasping the lower tray 104 while opening and closing separate components of the cassette 100. The tab 118 may be located, for example, proximate the back wall 110 of the upper tray 102 when the cassette 100 is assembled. Similarly, the cover 142 may include a tab 144 that is complementary to the tab 118 of the lower tray 104 for ease of grasping the cover 142 while opening and closing the separate components of the cassette 100. In some embodiments, the tab 118 of the lower tray 104 and the tab 144 of the cover 142 may be directly or partially aligned with one another. In other embodiments, the tab 118 of the lower tray 104 and the tab 144 of the cover 142 may not be aligned with one another, but may be proximate one another on the same side of the cassette 100. In yet other embodiments, the tab 118 of the base portion 116 and the tab 144 of the cover 142 may be located on opposite or adjoining sides of the cassette 100. In some embodiments, the upper tray 102 may also include a similar tab to facilitate assembly or disassembly of the cassette 100.

As shown in FIGS. 1-3, multiple (e.g., six) compartments 120 may be separated by dividers 126 extending from the front wall 108 to proximate the back wall 110 of the upper tray 102. By way of example, the tissue sample cassette 100 may include six compartments 120 for retaining respective tissue samples. In other embodiments, the tissue sample cassette 100 may include fewer or more compartments 120 (e.g., 4-12 compartments 120), depending on, for example, the size and shape of the compartments 120, the size and shape of the cassette 100, and/or the shape, quantity, and size of tissue samples to be collected from a patient in a particular procedure. For example, the quantity of compartments 120 may be selected to correspond to compartments of holders or trays (e.g., a matrix including a block of matrix material) for subsequent tissue processing. For example, a suitable matrix for receiving tissue samples for histological processing is disclosed in U.S. Patent Publication No. 2014/0135236 to Musat ("the '236 Publication"), which is assigned to the Assignee of this disclosure, and the disclosure of which is incorporated herein in its entirety by this reference. The '236 Publication discloses a matrix block that may be used in collecting and processing groups of six biopsies, for example. When such a matrix block is to be used for subsequent processing, a tissue sample cassette 100 according to this disclosure having six compartments 120 may be selected and utilized.

Each of the compartments 120 may have a proximal end portion 121 at or proximate the front wall 108 of the upper tray 102 and a distal end portion 122 proximate the back wall 110 of the upper tray 102. The compartments 120 may be sized, shaped, and configured to receive and retain respective tissue samples therein. In the embodiment shown in FIGS. 1-8, the compartments 120 may be arranged laterally between and substantially parallel to the first sidewall 112 and the second sidewall 114 of the upper tray 102 to retain tissue samples therein in a substantially horizontal orientation. Further, each of the compartments 120 may be elongated and separated by the dividers 126, which may also be elongated, to facilitate processing of tissue samples extracted during needle-core biopsy procedures. Alternatively, in additional embodiments, the compartments 120 may have a different shape (e.g., circular, square, rectangular, etc.) to accommodate tissue samples of different types (e.g., dermatological samples, shaves, punches, excisions, etc.), sizes, and shapes.

As used herein, the term "substantially" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

However, additional sizes and configurations of the compartments 120 and the dividers 126 are envisioned. For example, the compartments 120 may be rectangular, square, circular, or oval in shape and may be configured to facilitate tissue samples collected during procedures other than needle-core biopsy procedures. For example, the compartments 120 may be provided in different sizes and shapes, and the medical professional taking the biopsy may select the tissue sample cassette having the appropriate size and shape to accept a particular type, shape, and size of biopsy.

Referring again to FIGS. 1-3 and 7, the dividers 126 of the compartments 120 may also be arranged laterally between and substantially parallel to the first sidewall 112 and the second sidewall 114 of the upper tray 102. Inner sidewalls 128 of the dividers 126 may extend downward from the top wall 106 of the upper tray 102. In some embodiments, the inner sidewalls 128 may be substantially planar and vertical. In other embodiments, the inner sidewalls 128 of the dividers 126 may be nonplanar and/or angled. For example, the inner sidewalls 128 may be tapered or at least partially tapered to facilitate retention and retrieval of tissue samples retained in the compartments 120. In some embodiments, the inner sidewalls 128 may include multiple portions having differing slopes relative to one another. For example, the inner sidewalls 128 may include a lower vertical sidewall 128a, an inclined sidewall 128b, and an upper vertical sidewall 128c. By way of non-limiting example, each of the lower vertical sidewall 128a and the upper vertical sidewall 128c may be substantially vertical and transverse (e.g., perpendicular) with respect to the top wall 106 of the upper tray 102, while the inclined sidewall 128b may bridge the lower vertical sidewall 128a and the upper vertical sidewall 128c and may be oriented at an angle (e.g., between about 30° and 40°) with respect to the top wall 106 of the upper tray 102. Further, the lower vertical sidewall 128a may be about 1.5 mm in height above an upper surface of the absorbent material 134. Such a "tapered" configuration of the inner sidewalls 128 of the dividers 126 may facilitate retention and retrieval of the tissue samples. Further, retention and retrieval of the tissue samples may also be facilitated by the upper surface of the absorbent material 134 having a concave (e.g., domed) aspect in a lateral cross-section of each of the compartments 120, which concave shape may be obtained by the dividers 126 pressing down on the upper surface of the absorbent material 134 when the cassette 100 is assembled. Optionally, in some embodiments, an upper surface of the absorbent material 134 may include one or more cutouts 135, shown in FIG. 2 in dashed lines, to facilitate receipt and retention of tissue samples. The cutouts 135 may have one or more of various sizes and shapes, which may be selected to receive various tissue sample shapes and sizes. By way of example, the cutouts 135 may have a circular shape with a diameter selected to receive a dermatological punch biopsy of a predetermined size.

Each of the compartments 120 and the dividers 126 may extend across only a portion of the top wall 106 between the front wall 108 and the back wall 110 of the upper tray 102. For example, each of the compartments 120 and the dividers 126 may extend from at or proximate the front wall 108 while not fully extending to the back wall 110 of the upper tray 102. In other words, the compartments 120 and the dividers 126 may not extend to the back wall 110. Rather, an area of the top wall 106 between the distal end 122 of the compartments 120 and the back wall 110 may be reserved for identifiers 124 of the respective compartments 120. For example, alphanumeric indicators (e.g., Arabic numerals, letters) may be located on the top wall 106 between the distal end 122 of each of the compartments 120 and the back wall 110 of the upper tray 102, as shown in FIGS. 1-7. As shown in FIGS. 4-6, an outer surface of the identifiers 124 may be raised relative to an outer surface of the top wall 106 of the upper tray 102. However, the identifiers 124 may be placed in any configuration (e.g., location, position, or orientation) in order to facilitate identification and orientation of respective compartments 120 and may include any type of indicator (i.e., symbol) in order to uniquely identify each of the compartments 120 to facilitate tracking of biopsy source locations. In some embodiments, the identifiers 124 may be provided in another manner, such as by printing, applying printed adhesive decals (e.g., stickers), or forming recessed identifiers 124, for example. At present, a medical professional typically records a position of tissue samples either manually (i.e., hand-written labels) or electronically by utilizing computerized software, for example. In some embodiments, systems may be provided in order to facilitate tracking of extraction location using the identifiers 124. For example, a user may have access to computerized programs having serially listed fields (e.g., 1-6) corresponding to each of the compartments 120 for entering (e.g., typing, selecting an option from a menu or graphic, speaking the location into a microphone for voice-recognition processing) the corresponding extraction information. By way of non-limiting example, such computerized programs may include drop-down menus in user interface displays. The drop-down menus for each of the fields (e.g., 1-6) may include one or more selection options and a table having multiple fields to assist a user with assigning information to be synchronized with a database, which drop-down menus may contain commonly used biopsy information (e.g., extraction locations) for specified procedures.

In addition, the identifiers 124 and/or other such markers may be configured to indicate the orientation of the cassette 100 to ensure the same orientation thereof during various stages of processing, which may be beneficial in tissue sample collection procedures (e.g., sample collection procedures of gall bladder, prostate core biopsy, or transverse vessel samples) requiring an appropriate specimen orientation to be maintained for pathologic radiologic correlation. In some embodiments, a layout of the cassette 100 may mimic location and orientation of extraction locations, and the compartments 120 may be similarly oriented such that source extraction locations may match location and orientation (e.g., organ map) of at least some of the compartments 120 in the cassette 100.

In some embodiments, each of the compartments 120 may be characterized as "wells" and may optionally include an opening 130 (e.g., recess) defined by two opposing lower vertical sidewalls 128a and a bottom portion extending therebetween in the front wall 108 of the upper tray 102. The opening 130 may be sized and configured to facilitate insertion of a needle in a respective compartment 120 and to enable a user to pull the needle toward the proximal end 121 thereof while depositing a tissue sample (e.g., prostate) taken during a needle-core biopsy procedure. Further, the opening 130 may ensure orientation maintenance during such a procedure, given the accessibility of the compartments 120 through the opening 130 of the front wall 108, which provides unidirectional access of the needle.

In some embodiments, each of the first sidewall 112 and the second sidewall 114 may not be uniform in height between the front wall 108 and the back wall 110 of the upper tray 102. For example, each of the first sidewall 112 and the second sidewall 114 of the upper tray 102 may have a relatively greater height with respect to the base portion 116 of the lower tray 104 proximate the back wall 110 of the upper tray 102 and may have a relatively lesser height with respect to the base portion 116 of the lower tray 104 proximate the front wall 108 of the top tray 102. In other words, the top wall 106, including each of the compartments 120 and the dividers 126, may slope downward from the back wall 110 to the front wall 108 of the upper tray 102. Further, the sidewalls 138 of the lower tray 104 may be correspondingly sloped to accommodate the sloped surface of the upper tray 102. Such a sloped configuration may facilitate deposition and alignment of the tissue sample into each of the compartments 120. In addition, the sloped configuration may further facilitate automated imaging and processing (e.g., grossing) of the specimen, as discussed in further detail below. Further, the cover 142 may be sized and configured to correspond to the sloped configuration of the upper tray 102 and the lower tray 104.

In addition, the inner sidewalls 128 of the dividers 126 may include depth markers 132 (e.g., scribe lines) to facilitate measurement of the tissue samples. For example, the depth markers 132 may include generally horizontal lines, grooves, or marks extending substantially parallel to the top wall 106 and along the inner sidewalls 128 of the dividers 126 of one or more (e.g., each) of the compartments 120. The depth markers 132 may be located on one or both of the inner sidewalls 128 and may extend from proximate to the proximal end 121 to proximate the distal end 122 of the compartments 120. In some embodiments, the depth markers 132 may also include generally vertical lines or marks extending substantially perpendicular to the top wall 106 and from proximate the top wall 106 to proximate a base of the lower vertical sidewalls 128a of the inner sidewalls 128 of the dividers 126 of one or more (e.g., each) of the compartments 120. In yet other embodiments, an optical or imaging system may include a reticle grid in a lens thereof in addition to or instead of the depth markers 132. By way of non-limiting example, the depth markers 132 may include a 1 mm grid pattern to aid in sizing the tissue samples. The depth markers 132 may facilitate manual and/or automatic measurement of tissue samples. For example, horizontal lines or marks may be used to ascertain a height of a sample, while vertical lines or marks may be used to ascertain a length of a sample. Such measurements may be used, in turn, to determine an approximation of an area covered by the tissue sample.

In some embodiments, the top wall 106 of the upper tray 102, including the dividers 126 of the compartments 120, may be configured to be positioned above an upper surface of the absorbent material 134. In this configuration, the volume of liquid (e.g., formalin, RNA preservative, etc.) may be available to each of the compartments 120 such that an upper surface of the absorbent material 134 is proximate (e.g., in physical contact) with a lower edge of each of the compartments 120. By way of example and not limitation, an upper surface of the absorbent material 134 may be in direct physical contact with a lower edge of the lower vertical sidewalls 128a of the inner sidewalls 128 of the dividers 126. In this manner, the tissue sample cassette 100 may provide a single source of preservative fluid for the tissue samples without requiring the tissue samples to be suspended in fluid (e.g., formalin) during collecting, transporting, and/or processing of the tissue samples. At present, tissue samples are typically transported from a clinic to a laboratory using vessels (e.g., bottles) of formalin. Such processes typically require large amounts of fluid to float each tissue sample in individual bottles. Alternatively, trays (e.g., cassettes) are known in the art. Such trays are typically transported within bottles filled with formalin, or fluid courses or conduits pass between openings in the surfaces of the trays, which trays are typically filled with a fluid (e.g., formalin) at first use. Therefore, use of the cassette 100 including the absorbent material 134 (e.g., pre-wetted sponge) enables convenience of use while excluding the need to float tissue samples in fluid, to handle and use large amounts of fluid (e.g., formalin) and without requiring multiple individual bottles.

As shown in FIG. 2, the cover 142 may include indentations 146 in a top wall thereof. The indentations 146 may correspond to and be aligned with respective compartments 120 of the upper tray 102 to facilitate assembly of the tissue sample cassette 100 and to maintain orientation of the tissue samples within the compartments 120. For example, the indentations 146 of the cover 142 may be elongated and may extend from a front wall thereof to proximate a back wall thereof. For example, the cover 142 may include six individual indentations 146 corresponding to six respective compartments 120 of the upper tray 102. In addition, the indentations 146 may be separated by elongated portions of the cover 142 lacking indentations corresponding to respective dividers 126 of the compartments 120. In addition, the indentations 146 may include sidewalls configured to correspond to the size and shape of the inner sidewalls 128 of the dividers 126 and may be form fitted thereto. Further, the indentations 146 may be recessed to a designated depth to facilitate a lower portion thereof to be proximate (e.g., touching) an upper surface of the absorbent material 134 and/or an upper surface of the tissue samples to facilitate retention and alignment thereof within the respective compartments 120 and to inhibit the tissue samples from moving and/or falling out of the compartments 120 during transportation. In addition, an underside surface of the cover 142 may be treated with a hydrophobic material (e.g., NEVER-WET® hydrophobic coating products) commercially available through NeverWet, LLC of Lancaster, PA, to reduce (e.g., hinder or restrict) the tissue samples from adhering to the underside surface of the cover 142.

In addition, a water-tight or water-resistant seal may be created in the cassette 100, when assembled, to facilitate fluid retention in the absorbent material 134 during storage and transportation of the tissue samples. Further, at least a portion (e.g., an outer surface) of the absorbent material 134 may include a hydrophilic material to further facilitate fluid retention therein and to deter the absorbent material 134 from drawing moisture from the tissue sample during transportation and/or processing thereof. In some embodiments, all or portions of an unused tissue sample cassette 100 may be further sealed (e.g., shrink wrap, blister pack, etc.) to ensure fluid retention in the absorbent material 134 prior to first use. Further, the cover 142 may be sized and configured to accommodate the lower tray 104 of an additional cassette 100 to be placed thereon in a stacked arrangement. In other words, the cover 142 may be form fitted to nest within the lower tray 104 of the additional cassette 100.

As shown in FIG. 8, the lower tray 104 may include a lower surface 148 of the base portion 116. A tracking element 150 may be positioned in a recess or adhered to an outer surface of the lower surface 148. The tracking element 150 may be a machine- and/or human-readable device or label including, for example, a barcode label, a written (e.g., printed or hand-written) label, a serial number label, or multiple alternative types of tissue sample tracking elements. In some embodiments, the tracking element 150 may be configured to facilitate automatic reading thereof for entry into an automated system, which device or label may uniquely identify tissue samples and, by virtue of an identification code, may identify evaluation, processing, and/or tests to be conducted thereon. In some embodiments, the tracking element 150 may include a radio-frequency identification (RFID) tag. In other embodiments, the tracking element 150 may include a near field communication (NFC) device or other such machine-readable or electronically transferrable tracking device. Optionally, the cassette 100 may include a space (e.g., on the upper tray 102, on the lower tray 104, and/or on the cover 142) for positioning labels to identify, for example, each of the compartments 120. For example, a space may be provided adjacent to the identifiers 124 to affix or otherwise provide a label for each of the compartments 120. Such labels, if present, may identify information relating to the tissue sample in each of the respective compartments 120, such as orientation of the tissue sample, location on an organ from which the tissue sample was taken, etc.

The tracking element 150 may be positioned on the lower surface 148 as shown in the embodiment of FIG. 8 to facilitate tracking and identification of the cassette 100. The tracking element 150 may reduce the likelihood of misidentification of tissue samples within each of the cassettes 100, and may further provide additional information corresponding to the tissue samples (e.g., doctor notes, patient name, patient age, patient gender, type of tissue sample(s), processing instructions). Such additional information may be stored in a networked database and identified with an identification or serial number associated with the tracking element 150. Further, the tracking element 150 may be positioned to be read (e.g., scanned) by a reader associated with an imaging device, as discussed in further detail below. In other embodiments, a reader may or may not be associated with an imaging device, and the tracking element 150 may be used for orientation confirmation of the cassette 100. In addition, the tracking element 150 may be located on an exterior surface of any one of the upper tray 102, the lower tray 104, or the cover 142. The location of the tracking element 150 on the cassette 100 may, however, be determined by the relative position of the reader to the cassette 100 during processing. For example, the lower surface 148 of the lower tray 104 may be positioned above the reader while an upper surface of the cassette 100 (e.g., cover 142 or upper tray 102) may be positioned below an imaging device (e.g., camera) positioned and configured to capture images of the tissue sample through the upper surface of the cassette 100 during processing, as discussed in further detail below.

Figure 9:
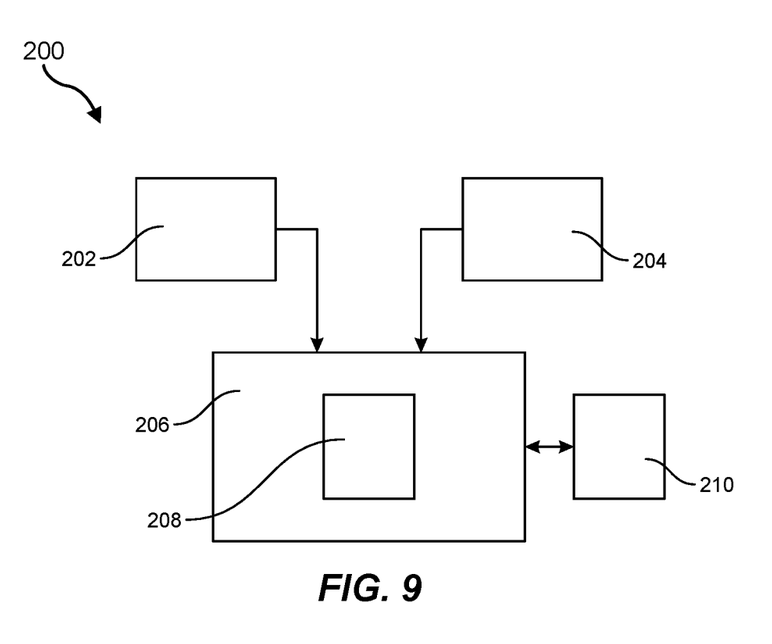
FIG. 9 is a simplified block diagram of an imaging system according to an embodiment of the disclosure.

FIG. 9 is a simplified block diagram of an imaging system 200 for automatically registering the tissue sample cassette 100 shown in FIGS. 1-8. The imaging system 200 may include an imaging device 202 (e.g., camera) to obtain images (e.g., monochrome or color) of tissue samples within the cassette 100. A tracking element reader 204 may be associated with the imaging system 200. The tracking element reader 204 may be positioned and configured to read (e.g., scan) the tracking element 150. The imaging system 200 may further include a processor 206 including memory 208 as well as a data storage unit 210 (e.g., external). The processor 206 may be in communication with each of the imaging device 202 and the tracking element reader 204.

As described in greater detail above, the tracking element reader 204 may be positioned to be below the lower surface 148 of the lower tray 104 to facilitate reading (e.g., scanning) of the tracking element 150 when the cassette 100 is presented for processing. The processor 206 may be configured to accept unique identification information from the tracking element 150 to enable processing (e.g., inputting, storing, classifying, etc.) information associated with records stored in the data storage unit 210.

The imaging device 202 may be positioned to be located above the cassette 100 for capturing one or more images (e.g., digital images) of the tissue samples when the cassette 100 is presented for processing. The imaging device 202 may be positioned and configured to obtain images from above, for example, with an optical axis of the imaging device 202 being transverse (e.g., perpendicular) to a surface (e.g., platform, table top, etc.) upon which the cassette 100 rests. In some embodiments, an optical axis of the imaging device 202 may not be located directly above, but may be positioned at a non-vertical angle with respect to the surface upon which the cassette 100 rests. For example, the imaging device 202 may be positioned to utilize the forward-sloping aspect of the cassette 100. The imaging device 202 may be equipped with an appropriate lens (e.g., camera lens) having a field-of-view adequate to view each of the compartments 120 of the cassette 100 in sufficient detail, including tissue samples placed therein. Further, the imaging device 202 may be configured for obtaining specific dimensions (e.g., height, length, area, etc.) of tissue samples. In some embodiments, the imaging device 202 may include one or more specialized cameras (e.g., 3D camera), multiple cameras at various angles, and/or various lighting conditions to assist in obtaining the measurements of the tissue samples. Such measurements may be obtained with the aid of the depth markers 132, as described above.

In addition, holding trays may be utilized within the imaging system 200 to facilitate processing of the tissue samples within the cassette 100. For example, the holding trays may provide a structure to aid in positioning the cassette 100 during processing (e.g., scanning, imaging, etc.) to facilitate the automated processing thereof. In other words, the holding trays may be utilized to promote proper alignment of the cassette 100 with the tracking element reader 204 and/or the imaging device 202. In addition, the holding trays may be sized and configured to accommodate known trays and cassettes of any source and/or configuration to facilitate processing by the imaging system 200. In this manner, in some embodiments, tissue samples may be automatically registered as part of the grossing processing without requiring the use of the particular cassette 100 disclosed above.

Images of tissue samples obtained by the imaging device 202 may then be received and stored in the memory 208 of the processor 206. The memory 208 may include or be associated with an algorithm (e.g., artificial intelligence, deep learning) configured to recognize (e.g., identify) tissue samples based on the captured images. The algorithm may be trained to accurately recognize the tissue samples and to calculate gross measurements thereof. One or more deep-learning algorithms may be trained using particular attributes of selected tissue samples stored in the memory 208 and/or the data storage unit 210. For example, such deep-learning algorithms may be trained using at least a portion of the attributes of current and/or previous tissue samples or using provided information, such as from an external database, for example. The trained deep-learning algorithms may be used by the processor 206 to render measurements of the tissue samples. For example, the algorithms may process the captured images using the processor 206 to discern the tissue samples from a background (e.g., materials of the cassette 100) for accurate locating and dimensioning of the tissue samples. In other embodiments, the algorithms may be utilized to recognize certain aspects of specific tissue samples. Information obtained from determining the measurements (e.g., height, length, area) of the tissue samples may then be used as part of the required gross description thereof. In this manner, the imaging system 200, including the processor 206, may provide gross measurements as well as one or more images of the tissue sample captured by the imaging device 202.

In some embodiments, the cassette 100 of this disclosure may facilitate and improve the process of obtaining gross measurements described herein by maintaining the tissue samples in substantially consistent and known orientations relative to the features of the cassette 100. The algorithms may be configured to identify the features of the cassette 100 from the images obtained by the imaging device 202 and to distinguish the tissue samples from and compare portions of the tissue samples to those features. Accordingly, the cassette 100 may enable improved and more efficient tissue sample detection and gross measurements thereof, potentially including depth measurements and measurements of multiple tissue samples in a single cassette 100.

The gross measurements and/or images may then be associated with records (e.g., patient records) stored in the memory 208 and/or the data storage unit 210. The algorithm stored within the memory 208 of the processor 206 may then provide a written description, which may or may not include discrete values of the measurements, and/or a visual representation of the measurements as a portion of the grossing process. The automated grossing process includes steps to identify regions (e.g., the identifiers 124, the depth markers 132, etc.) of the cassette 100, to recognize the tissue samples, and to associate the gross measurements thereof with one or more of the identified regions of the cassette 100. Such a process enables linking the collected tissue samples, utilizing the identified regions of the cassette 100, with one or more distinct collections of tissue samples (e.g., known tissue samples). In some embodiments, utilizing multiple images with varying lighting conditions may increase accuracy of the deep-learning algorithm. Further, additional pre-processing and post-processing steps may allow the images to be normalized and smoothed to produce results consistent with the needs of the user.

In use, the tissue sample cassette 100 may be utilized in a tissue-collection procedure (e.g., needle-core biopsy) performed at a clinic or other medical facility. To prepare the cassette 100 for use, each of the tab 144 of the cover 142 and the tab 118 of the lower tray 104 may be grasped and pulled in opposite directions to remove (e.g. detach) the cover 142 from each of the upper tray 102 and the lower tray 104, which may remain assembled to one another, retaining the absorbent material 134 therebetween. The identifiers 124 of the compartments 120 may indicate a proper orientation in which to place the cassette 100 during the procedure. Further, the identifiers 124 may be used to track locations and orientations of harvested tissue samples, as described in greater detail above.

One or more tissue samples may be collected from a patient during the procedure and the collected tissue samples may then be placed within respective compartments 120 of the cassette 100. For example, tissue samples (e.g., prostate samples) taken from a patient during a biopsy procedure may be deposited within the respective compartments 120. As the tissue samples are deposited into the respective compartments 120, information associated therewith may be logged into an anatomic pathology system (e.g., manually or automatically) to facilitate inputting and tracking of such information. For example, computerized programs including fields (e.g., utilizing drop-down menus, graphics, etc.) for entering the corresponding extraction information may be utilized. In addition, the tracking element 150 may facilitate linking the extraction information of collected tissue samples contained within the cassette 100 with respective patients, organs, and/or procedures.

Following the biopsy procedure, the cassette 100 may be reassembled by replacing the cover 142 and ensuring a tight seal by utilizing each of the tab 144 of the cover 142 and the tab 118 of the lower tray 104, for example. During transportation and subsequent processing, the absorbent material 134 (e.g., pre-wetted sponge) may maintain moisture within the cassette 100 for an extended period of time prior to first use and during transportation and/or processing of the collected tissue samples. The tissue sample cassette 100 may then be transported to a pathology laboratory for further processing (e.g., grossing) of the collected tissue samples using the imaging system 200, including the imaging device 202 and/or the tracking element reader 204. In some instances, the cassettes may not be transported to a laboratory for the grossing procedure. Rather, the grossing procedure may be performed at the clinic or medical facility (e.g., the point-of-care) using an on-site imaging system 200. The cassette 100 may then be transported to a pathology laboratory for further processing (e.g., diagnostic studies) once the grossing process has been completed at the location where the biopsy was taken. In some embodiments, information obtained by the imaging system 200 may be presented to a pathologist for review. The pathologist may review the image(s) obtained by the imaging system 200, and may provide additional gross measurements or testing to manually complete the grossing process. In addition, the pathologist may be able to provide an improved analysis (e.g., diagnosis) of the tissue sample by reviewing the image(s) of the tissue sample as the tissue sample was taken at the clinic or medical facility. Tissue sample attributes may change during transportation from the clinic or medical facility to a laboratory. Accordingly, providing the image(s) of the tissue sample taken at the clinic or medical facility in a standardized platform (e.g., in the cassette 100) may facilitate pathological procedures and improve patient care.

One or more cassettes 100 may be presented to initiate the automated grossing process using the imaging system 200. The tracking element 150 may be read (e.g., scanned) with the tracking element reader 204. In some embodiments, the cassette 100 may be positioned and/or passed (e.g., swiped) over the tracking element reader 204 positioned below the lower tray 104 of the cassette 100. In addition, the tissue samples may be presented for imaging using the imaging device 202 by aligning the cassette 100 with the imaging device 202 positioned proximate (e.g., above) the cassette 100. In some embodiments, the cover 142 may be removed prior to obtaining images. In other embodiments, the cover 142 may be clear (e.g., transparent) to facilitate imaging therethrough. The sloped aspect of the cassette 100 may facilitate the imaging process. In some embodiments, reading the tracking element 150 with the tracking element reader 204 and imaging the cassette 100 with the imaging device 202 may be done substantially at the same time (e.g., simultaneously). In other embodiments, the reading of the tracking element 150 and the imaging of the cassette 100 may not be done at the same time, but may be done before or after one another. Further, positioning the cassette 100 within the imaging system 200 may be done manually by a user and/or by using an automated process for handling the cassette 100 and/or initiating the grossing process. In some embodiments, the cassette 100 and/or known trays or cassettes may be placed in holding trays prior to processing with the imaging system 200. In such configurations, the tracking element 150 may or may not be associated with the holding trays rather than the individual cassette 100.

Once the cassette 100 is positioned proximate the imaging device 202, the imaging device 202 (e.g., camera) may capture images of the tissue samples disposed within the compartments 120 of the cassette 100. One or more images (e.g., digital images) may be obtained during the grossing process, as described in greater detail above. If needed, the cover 142 may then be reassembled with the lower tray 104 and the cassette 100 may be stacked or otherwise packaged for transportation and/or further processing. The captured images of the tissue samples may be linked with electronic records (e.g., patient records) associated with the tracking element 150. The processor 206 using the deep-learning algorithm may then be utilized to recognize the tissue samples and to calculate gross measurements, as described in greater detail above. Once the grossing process has been completed, the gross measurements and images of the tissue samples may be associated with individual electronic records and utilized during subsequent processing, diagnosing, and/or reporting.

The following description provides specific details, such as material types, manufacturing processes, uses, and structures in order to provide a thorough description of embodiments of the disclosure. However, a person of ordinary skill in the art will understand that the embodiments of the disclosure may be practiced without employing these specific details. Indeed, the embodiments of the disclosure may be practiced in conjunction with conventional manufacturing techniques and materials employed in the industry.

In the preceding detailed description, reference is made to the accompanying drawings, which form a part hereof, and in which is shown, by way of illustration, specific embodiments in which the disclosure may be practiced. These embodiments are described in sufficient detail to enable a person of ordinary skill in the art to practice the disclosure. However, other embodiments may be utilized, and structural, procedural, and other changes may be made without departing from the scope of the disclosure. The illustrations presented herein are not meant to be actual views of any particular system, device, structure, or process, but are idealized representations that are employed to describe the embodiments of the disclosure. The drawings presented herein are not necessarily drawn to scale. Similar structures or components in the various drawings may retain the same or similar numbering for the convenience of the reader; however, the similarity in numbering does not mean that the structures or components are necessarily identical in size, composition, configuration, or other property.

As used herein, any relational term, such as "first," "second," "top," "bottom," "upper," "lower," "front," "back," "above," "below," "horizontal," "vertical," etc., is used for clarity, consistency of terminology, and convenience in understanding the disclosure and accompanying drawings and does not connote or depend on any specific preference, orientation, or order, except where the context clearly indicates otherwise. For example, the disclosure includes tissue sample cassettes that may be rotated or flipped in use such that the top thereof faces down and the bottom thereof faces up, and/or the front faces away from the user and the back faces toward the user. Thus, while one example orientation of tissue sample cassettes is used herein for clarity, other possible orientations are contemplated by, and are included in, the disclosure.

The embodiments of the disclosure described above and illustrated in the accompanying drawing figures do not limit the scope of the invention, since these embodiments are merely examples of embodiments of the disclosure. The invention is encompassed by the appended claims and their legal equivalents. Any equivalent embodiments lie within the scope of this disclosure. Indeed, various modifications of the disclosure, in addition to those shown and described herein, such as other combinations and modifications of the elements described, will become apparent to those of ordinary skill in the art from the description. Such embodiments, combinations, and modifications also fall within the scope of the appended claims and their legal equivalents.

What is claimed is:

1. A tissue sample container, comprising:
    a lower tray including a base portion;
    an absorbent substrate positioned over the base portion of the lower tray;
    dividers defining compartments over the absorbent substrate, the compartments sized and configured for retention of respective tissue samples; and
    a cover configured to, when closed over the lower tray and the absorbent substrate, hold at least one tissue sample in place over and relative to the absorbent substrate in at least one corresponding tissue-receiving compartment formed by the dividers and between the absorbent substrate and the cover.

2. The tissue sample container of claim 1, wherein the absorbent substrate comprises a sponge.

3. The tissue sample container of claim 1, wherein the absorbent substrate is wetted with a liquid, wherein the liquid comprises a preservative.

4. The tissue sample container of claim 3, wherein the preservative comprises an RNA preservative.

5. The tissue sample container of claim 3, wherein the liquid comprises a fixative.

6. The tissue sample container of claim 5, wherein the fixative comprises formalin.

7. The tissue sample container of claim 1, further comprising an upper tray shaped and sized to be positioned over the lower tray and the absorbent substrate and under the cover when the cover is closed over the lower tray and the absorbent substrate.

8. The tissue sample container of claim 7, wherein the upper tray comprises a top wall including the dividers.

9. The tissue sample container of claim 8, wherein the upper tray comprises identifiers for the respective compartments.

10. The tissue sample container of claim 9, wherein the identifiers comprise alphanumeric indicators.

11. The tissue sample container of claim 8, wherein the top wall includes openings in a front wall of the upper tray, wherein the openings are sized and configured to facilitate insertion of needles in the respective compartments for depositing needle-core biopsies in the compartments.

12. The tissue sample container of claim 1, wherein the compartments comprise between four and twelve compartments.

13. The tissue sample container of claim 1, further comprising a tracking element on the lower tray for uniquely identifying the tissue sample container.

14. A method of forming a tissue sample container, the method comprising:
    positioning an absorbent substrate over a base portion of a lower tray;
    positioning dividers to define compartments over the absorbent substrate, the compartments sized and shaped for retention of respective tissue samples; and
    releasably securing a cover over the absorbent substrate and the lower tray, the cover including indentations corresponding to the compartments defined over the absorbent substrate.

15. The method of claim 14, wherein the absorbent substrate comprises a sponge.

16. The method of claim 14, wherein the indentations touch an upper surface of the absorbent substrate when the cover is closed.

17. The method of claim 14, further comprising treating an underside of the transparent cover with a hydrophobic material.

18. The method of claim 14, further comprising positioning an upper tray over the absorbent substrate and the lower tray prior to releasably securing the cover over the substrate and the lower tray.

* * * * *